(12) United States Patent
Eshelman et al.

(10) Patent No.: US 6,774,795 B2
(45) Date of Patent: Aug. 10, 2004

(54) ELECTRONIC ASSISTANT INCORPORATED IN PERSONAL OBJECTS

(75) Inventors: Larry J. Eshelman, Ossining, NY (US); Srinivas Gutta, Buchanan, NY (US); Hugo J. Strubbe, Yorktown Heights, NY (US); John Milanski, Louisville, CO (US)

(73) Assignee: Koninklijke Philips Electroncs N.V., Eindhoven (NL)

( * ) Notice: Subject to any disclaimer, the term of this patent is extended or adjusted under 35 U.S.C. 154(b) by 200 days.

(21) Appl. No.: 09/895,146

(22) Filed: Jun. 30, 2001

(65) Prior Publication Data

US 2003/0001742 A1 Jan. 2, 2003

(51) Int. Cl.[7] .............................................. G08B 23/00
(52) U.S. Cl. ................... 340/573.1; 340/539.1; 340/539.11; 340/539.12; 340/539.13; 600/301; 379/38; 379/40; 379/45; 379/51; 455/100
(58) Field of Search ........................ 340/573.1, 573.4, 340/539.1, 539.11, 539.12, 539.13, 540; 600/301, 306; 379/37, 38, 39, 40, 41, 42, 45, 51; 455/100

(56) References Cited

U.S. PATENT DOCUMENTS

| | | | |
|---|---|---|---|
| 4,829,285 A | * 5/1989 | Brand et al. | 340/573.1 |
| 5,086,391 A | * 2/1992 | Chambers | 340/573.1 |
| 5,554,975 A | * 9/1996 | Hall et al. | 340/573.7 |
| 5,662,123 A | 9/1997 | Goldman | 128/782 |
| 5,670,944 A | * 9/1997 | Myllymaki | 340/573.1 |
| 5,729,203 A | * 3/1998 | Oka et al. | 340/573.1 |
| 6,102,856 A | * 8/2000 | Groff et al. | 600/301 |
| 6,147,618 A | * 11/2000 | Halleck et al. | 340/669 |
| 6,163,249 A | * 12/2000 | Betcher, III | 340/407.1 |
| 6,198,394 B1 | * 3/2001 | Jacobsen et al. | 340/573.1 |
| 6,239,700 B1 | * 5/2001 | Hoffman et al. | 340/539 |
| 6,265,978 B1 | * 7/2001 | Atlas | 340/575 |
| 6,333,694 B2 | * 12/2001 | Pierce et al. | 340/573.1 |
| 6,349,201 B1 | * 2/2002 | Ford | 455/404 |
| 6,433,690 B2 | * 8/2002 | Petelenz et al. | 340/573.1 |
| 6,496,111 B1 | * 12/2002 | Hosack | 340/540 |

FOREIGN PATENT DOCUMENTS

| | | | |
|---|---|---|---|
| DE | 29919839 U | 3/2000 | A61B/5/11 |
| DE | 19911766 A | 9/2000 | A61B/5/00 |
| WO | 9945516 A1 | 9/1999 | G08B/25/01 |
| WO | 0107993 A1 | 2/2001 | G06F/1/16 |

* cited by examiner

*Primary Examiner*—Nina Tong

(57) ABSTRACT

An electronic assistant, incorporates electronic functions in a personal object that the user finds indispensable. Examples of personal objects include a cane, a walking stick, a walker, a wheelchair, a personal transportation vehicle, a purse, a key holder, a watch, a pendant, a hearing aid, an eyeglass frame, or a crutch. Electronics may include a PDA, a cell phone, a navigation module, a biosensor module, and an emergency alert module. The navigation module might include a GPS, an altimeter, an electronic compass, and/or a stored map. Biosensors may be directly incorporated into the personal device or communicate with a receiver therein if the biosensor is required to be attached directly to the user's body or surgically implanted. The emergency alert module may include an emergency button, and an emergency notification sequence stored in the electronic assistant capable of calling for assistance through the cell phone.

10 Claims, 3 Drawing Sheets

ELECTRONIC ASSISTANT INCORPORATED IN PERSONAL OBJECTS

BACKGROUND OF THE INVENTION

1. Field of the Invention

The invention relates to devices with combinations of features that assist people with disabilities in their health monitoring, communication, organization, and navigation needs.

2. Background

As important as electronic devices have become in most people's daily lives, they can be difficult to use for some major segments of the population. For example, the elderly and persons with mild disabilities. Also persons with little or no experience in the operation of electronic devices often find it difficult to develop the habit of using such devices.

SUMMARY OF THE INVENTION

Personal objects are, for the purposes of this application, items that a person, by habit or necessity, finds indispensable and, consequently, keeps constantly on their person or within easy reach.

Personal objects that are used to improve their lifestyle or cope with a disability, form a base upon which the present invention is built. Examples of personal objects include: canes, hats, tobacco tins, jackets, datebooks, pill boxes, knitting bags, pocketbooks, eyeglass cases, walkers, and orthotic appliances. It is a goal of the invention to provide an electronic assistant that is integrated into the personal object in a manner that augments or improves the standard function of the personal object and insures the electronic assistant is never far away. The functional features of the electronic assistant may include:

Communication functions, such as a cell phone, pager, radio transceiver, emergency pager/alert device, etc.;

Health monitoring functions, such as heart rate, blood pressure, electrocardio profile, skin conductivity, eye function, chemical or drug concentration, etc.;

Organization functions, such as those functions commonly found in a personal digital assistant (PDA); and Navigation functions, such as provided by a global positioning system, compass, barometric altimeter, etc.

The device's input interface can be manual, radio frequency, infrared, voice, hard-wire, etc., the output interface can be visual, auditory, etc., and input/output can be either direct or indirect via attached hardware.

It is another object of the invention to provide an electronic assistant, comprising; a personal object having at least one electronic module incorporated therein, and each electronic module is selected from the group of consisting of a PDA, a cell phone, a navigation module, a biosensor module, and an emergency alert module.

It is another object of the present invention to provide an electronic assistant, comprising; a personal object having at least one electronic module incorporated therein. The personal object is one of a cane, a walking stick, a walker, a wheelchair, a personal transportation vehicle, a purse, a key holder, a watch, a pendant, a hearing aid, an eyeglass frame, and a crutch. Each electronic module is selected from the group of consisting of a PDA, a cell phone, a navigation module, a biosensor module, and an emergency alert module. The PDA includes storage and retrieval of appointments and at least one of addresses, phone numbers, calendar events, memos, and to-dos and other lists. The navigation module includes at least one of a GPS, an altimeter, an electronic compass, and a stored map. The biosensor module includes; at least one biosensor, a biosensor information processor, and at least one biosensor communication channel connecting each biosensor with the biosensor information processor. Each biosensor is one of; a biosensor disposed on a surface of the personal object, a remote biosensor attached to the body of the user, and a remote biosensor surgically implanted in the body of the user. The biosensor communication channel is at least one of; a wire, a radio frequency transmitter and receiver, and an infrared transmitter and receiver. The emergency alert module includes an emergency button, and an emergency notification sequence stored in the electronic assistant capable of calling for assistance through said cell phone.

In summary the present invention is an electronic assistant, capable of overcoming a person's resistance to using electronic devices by incorporating electronic functions in a personal object that the user finds indispensable. Other examples of personal objects include a walking stick, a wheelchair, a personal transportation vehicle, a purse, a key holder, a watch, a pendant, a hearing aid, an eyeglass frame, and a crutch. Some examples of assistant electronics to be integrated with the personal object include a PDA, a cell phone, a navigation module, a biosensor module, and an emergency alert module. The PDA can include storage and retrieval of appointments, phone numbers, calendar events, memos, and to-dos & other lists. The navigation module might include a GPS, an altimeter, an electronic compass, and/or a stored map. Biosensors may be directly incorporated into the personal device or communicate with a receiver therein if the biosensor is required to be attached directly to the user's body or surgically implanted. The emergency alert module may include an emergency button, and an emergency notification sequence stored in the electronic assistant capable of calling for assistance through the cell phone.

The invention will be described in connection with certain preferred embodiments, with reference to the following illustrative figures so that it may be more fully understood. With reference to the figures, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DETAILED DESCRIPTION OF THE PREFERRED EMBODIMENTS

Figure 1:
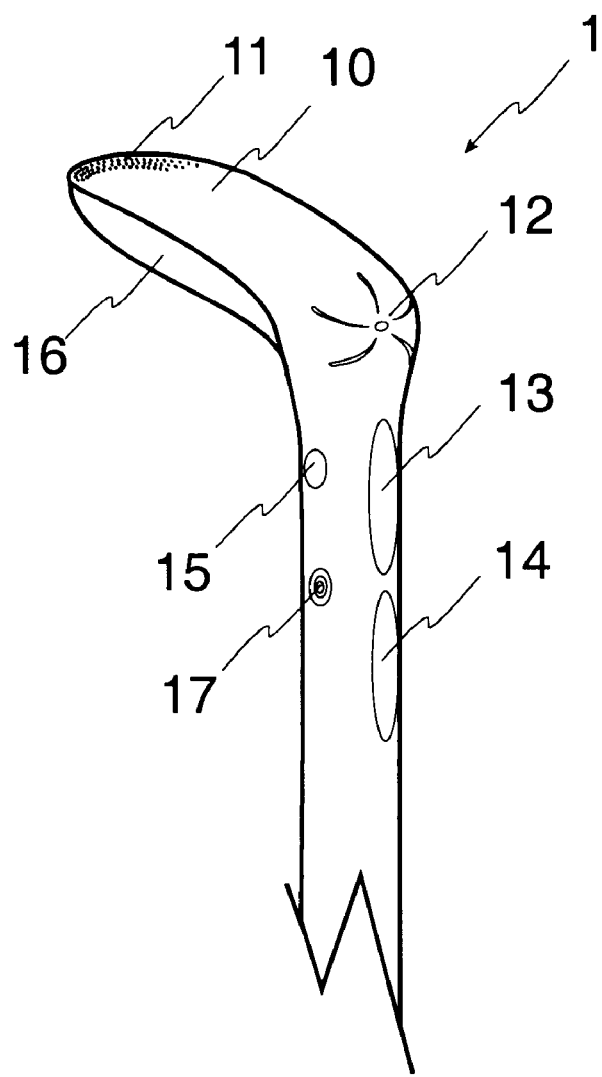
FIG. 1 is a perspective view of an embodiment of the present invention showing a cane handle as an example of a personal object with the electronic interface features illustrated.

Referring to FIG. 1, a personal object 1, shown here by example as a cane or walking stick, is any object that a person, by habit or necessity, finds indispensable and, consequently, keeps constantly on their person or within easy reach. Another feature of at least some personal objects is that they are in contact with the person regularly, so that a biosensor 16 integrated into them may regularly receive inputs to monitor the health status of the user. Other examples of personal objects were identified in the Summary of the Invention section and include: walkers, wheelchairs, crutches, personal transportation vehicles, watches, key holders, purses, glasses, hearing aids, etc.

The personal object 1, in the example embodiment, has a housing 10 encasing the electronic components of a digital assistant. Here the housing 10 forms the handle of the cane. In the present example, a speaker 11, and a microphone 12 are used to generate a user interface, allowing the user to make use of the assistant by speaking and listening. Additionally and/or in combination with the microphone 12/speaker 11 interface, the user can command the assistant by operating scroll button 13 and/or enter button 14 for scrolling through and selecting from recorded menus, and/or entering verbal data. An emergency button 15 may also be provided.

The biosensor module 16 may be incorporated directly into the portion of housing 10 so that sensors comes in direct contact with the user's skin. Alternatively, the sensor may be remote, such as a heart monitor chest strap, and communicate with a component integrated in the housing 10, or example by a radio frequency or infrared link.

An accessory port 17 may be provided to interface indirectly or upload or download data and may allow connection to a keyboard, computer, keypad, modem, display, etc. The port 17 may be an infrared, radio wireless, cable-type connector, or any other suitable data channel device.

Figure 2:
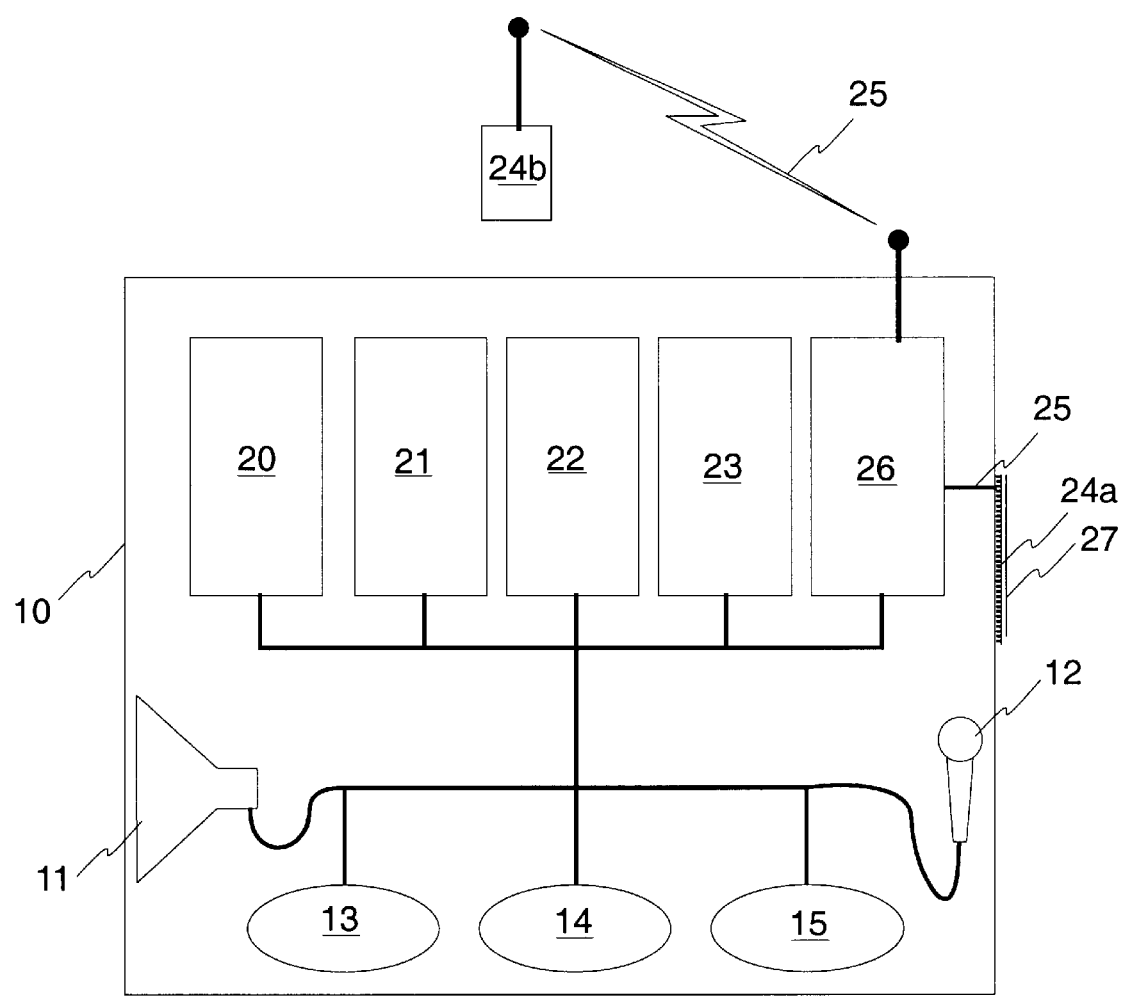
FIG. 2 is a functional block diagram illustrating a possible combination of integrated electronic components consistent with an embodiment of the present invention.

Referring to FIG. 2, the integrated electronic functions in housing 10 include a personal digital assistant (PDA) 20. PDA 20 stores and retrieves appointments and may be programmed to store and retrieve addresses and phone numbers, calendar events, and memos, to-do lists, etc. Additionally, PDA 20 functionality may include any other capabilities known to be used in PDA applications.

PDA 20 may be operable without a visual display relying solely, or primarily upon, speech recognition and synthetic speech output, though a display may be made attachable through port 17. Speech (or other audio symbology) is output from PDA 20 to the user is through speaker 11 in the form of synthesized speech or replayed sound samples. Direct user input may be through a microphone 12. Speech recognition may be used to enter data such as phone numbers, addresses, memos, appointments, activate functions such as entering commands or parameters, call for help, etc.

Integrated with PDA 20 in housing 10 is a cell phone 21. Cell phone 21 utilizes microphone 12 and speaker 11 for communication with others via cell phone carrier networks. Additionally, dialing functions of numbers stored in the PDA 20 may automatically be retrieved and used to program cell phone 21 responsively to voice commands. Of course, dialing of non-stored numbers may also activated by speaking numbers into microphone 12 according to known techniques.

A navigation function 22 integrates with PDA 20 to provide navigation information to the user. A GPS feature of navigation function 22 determines the user's present position. Cartographic information is stored in PDA 20 and the user's present position assessed in relation to addresses, appointments, distances, directions for the best route, travel times, etc.

For example, say the user lives uptown, has a haircut appointment across town, followed by a doctor's appointment downtown. The PDA may be programmed to calculate, based on the user's then-current position, the distance, route, and mode of transportation; then sound a reminder and instructions sufficiently in advance of each appointment time to allow preparation and travel. If the user appears to be headed in the wrong direction, the PDA may generate a local warning signal and if the user remains off track, a remote signal to a helper via the cell network.

Integrated with PDA 20, cell phone 21, and navigation function 22 within housing 10 is a biosensor module 16. Biosensor module 16 includes biosensor (s) 24a and/or 24b, biosensor communication channel 25, and biosensor information processor 26.

Biosensors 24a are those incorporated into housing 10's surface and include a skin contact detector 27 to activate biosensing. Biosensors 24a are capable of monitoring biological processes measurable on the user's skin. For example, pulse, temperature, galvanic skin response, vibration, moisture, force, etc. These parameters can be supplied to a classification engine on board the PDA, which may be programmed to combine them and detect danger zones in a parameter space. So, for example, if force and vibration are high, the PDA may be programmed to transmit a remote message to a caretaker indicating that the user is struggling, for example with weakness or palsy. In addition, the biosensor parameter space may be combined with other measurable parameters in such a user-state classification engine to increase the reliability or sensitivity of state detection.

Biosensors 24b are remote from housing 10 and may constantly monitor relevant biological processes. Biosensors 24b may be capable of monitoring various pathognomonic biological processes. For example, the biosensors 24b may include a halter monitor (attached to the chest) providing the user's electrocardiogram. The PDA may be programmed to classify risk zones in the parameter space. Remote biosensor 24b may also be a surgically implanted device used to monitor blood gas level, blood pH, blood insulin or blood glucose level, histamine level, specific enzyme level, prescription drug concentration, etc. Alternatively a pressure transducer placed appropriately in a cast may monitor stresses placed on the broken limb as the patient progresses toward healing.

Biosensor communication channel 25 connects biosensors 24a and 24b to biosensor information processor 26. Biosensor communication channel 25 may take the form of any suitable communication channel including a hard-wired connection (preferable in the case of an integral biosensor 24a) or in the form of an RF or infrared transmitter/receiver set in the case of a remote type biosensor 24b.

Biosensor information processor 26 receives raw data from biosensor 24a or 24b, through biosensor communication channel 25, and classifies the user state. Next, the state class is used to generate a useful output such as a call to a caretaker or a message. For example, if the data is to be used in a biofeedback type situation, biosensor information processor 26 may be programmed to provide a proportional signal to the user through speaker 11. If the state exceeds some threshold, an audio message may be generated, for example: "your blood glucose is high, take your insulin now", "you are putting too much weight on your leg", "your heart rate is exceeding your prescribed limit, please reduce your activity level now", etc.

Biosensor monitoring may also be integrated, along with PDA 20, cell phone 21, and navigation function 22, within housing 10, to emergency alert 23 including emergency button 15. Raw data indicating an emergency condition causes biosensor information processor 26 to activate an emergency alert sequence stored in PDA 20 to notify, via cell phone 21, specific individuals or organizations of the emergency situation and request assistance. The user's location and navigation instructions thereto provided by navigation function 22 can also be programmed to be automatically provided.

Additionally, emergency alert 22 may also be activated by the user by simply pressing emergency button 15, whereby the user can either speak directly to the answering party(ies) using cell phone 21 or a predetermined emergency message may be sent.

Figure 3:
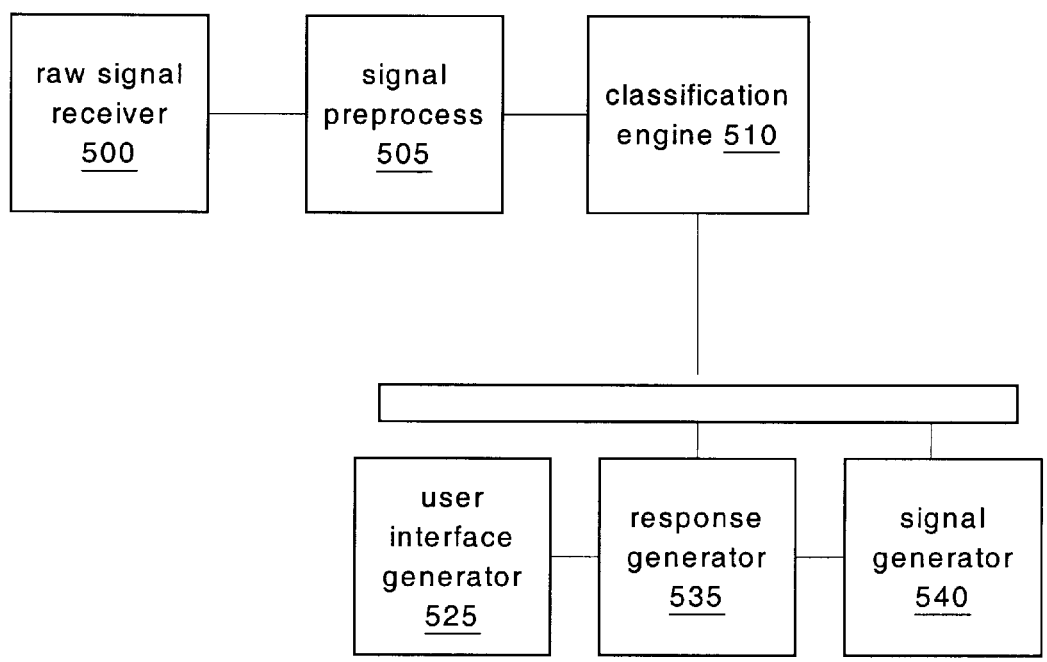
FIG. 3 is a functional block diagram of information flow in a processor controlling and processing data for a digital assistant according to an embodiment of the invention.

Referring now to FIG. 3, the raw signals received 500 from the biosensors, GPS, inputs, audio input, and any other data sources may be preprocessed 505 and applied to a classification engine 510. For example, the classification engine may recognize the normal spoken voice of the user and convert the speech into command or verbal symbols for interpretation. It may generate a user state indicator based on an input vector that includes all the raw data input. Unrecognized audio or audio classified as being consistent with struggling or injury may also form part of an input vector and used to classify the user state. The classification engine 510 may operate based on known network techniques such as Bayesian and neural networks. The fit between input vectors and responses may be provided by a weighted factor template as in a Bayesian network (or neural network or other machine-intelligence technique).

The output of classification engine 510 is a user state vector that may be used by a response generator process 535 running on the PDA or any other controller associated with the intelligent assistant. The response generator receives inputs and sends outputs through a user interface generator process 525. A signal generator process 540 may transmit signals through output ports or wireless channels. For example, the signal generator process 540 may generate phone calls with synthetic or recorded speech messages or emit alarm signals.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. An electronic assistant, comprising:

a non-electronic personal object that is adapted to assist a user's mobility, wherein said non-electronic personal object having an electronic module incorporated therein, said electronic module being adapted for communicating and monitoring certain physiological attributes of a user while said non-electric personal object is in use and being in contact with a user, and wherein said non-electronic personal device further comprises a user interface cooperative with the communicating and monitoring said non-electronic personal object having a utility beyond that of the electronic module incorporated therein, wherein said electronic module monitors predetermined physiological data of a user while said user is at least in physical contact with the non-electronic personal object and said electronic module activates a call for assistance when a selected physiological data being monitored falls below a predetermined threshold after a predetermined amount of time.

2. The electronic assistant of claim 1, wherein said non-electronic personal object is one of a cane, a walking stick, a walker, a wheelchair, a personal transportation vehicle, and a crutch, or any combination of the same and the electronic module is further adapted for organizing and navigating.

3. The electronic assistant of claim 2, wherein said electronic module has a GPS receiver and said PDA is programmed to generate a user state indication responsively to a location signal from said GPS receiver.

4. The electronic assistant of claim 1, wherein said non-electronic personal object is one of a cane and a walking stick.

5. The electronic assistant of claim 1, wherein said electronic module has a personal digital assistant (PDA) with a first biosensor, said PDA programmable to classify user status responsively to a signal from said first biosensor.

6. The electronic assistant of claim 5, a second biosensor, and said PDA is further programmed to combine signals from said first and second biosensors to derive a user state indication responsively to both said signals.

7. The electronic assistant of claim 1, wherein said electronic module further comprises a biosensor with a receiver for wirelessly receiving biosensor signals from one or more sensors.

8. The electronic assistant of claim 7, wherein said one or more sensors are in contact with one of the body of said user and surgically implanted within the body of said user.

9. The electronic assistant of claim 1, wherein said electronic module has an emergency alert system for transmitting an emergency notification sequence signaling a need for assistance.

10. An electronic assistant, comprising:

a non-electronic personal object that is adapted to assist a user's mobility, said object having an electronic module incorporated therein and a user interface associated therewith, said non-electronic person object having a utility beyond that of the electronic module incorporated therein and said electronic module monitors certain physiological attributes of a user while said non-electric personal object is in contact with the user during use, wherein said non-electronic personal object being one of a cane, a walking stick, a walker, a wheelchair, a personal transportation vehicle, a key holder, a watch, a hearing aid, an eyeglass frame, and a crutch;

said at least one electronic module including a biosensor module, an emergency alert module and a new navigation module, and optionally includes at least one of a personal digital assistant (PDA), and a cell phone;

said navigation module having at least one of a GPS, an altimeter, an electronic compass, and a stored map;

said biosensor module having at least one biosensor, a biosensor information processor, and at least one biosensor communication channel connecting each said at least one biosensor with said biosensor information processor;

each said at least one biosensor being one of a biosensor disposed in a surface of said personal object, a remote biosensor attached to the body of the user, and a remote biosensor surgically implanted in the body of said user;

said biosensor communication channel being at least one of a wire, a radio frequency transmitter and receiver, and an infrared transmitter and receiver; and said emergency alert module having an emergency button, and an emergency notification sequence stored in said electronic module adapted for calling for assistance through said cell phone.

* * * * *